United States Patent [19]

Tonomura et al.

[11] Patent Number: 5,601,588
[45] Date of Patent: Feb. 11, 1997

[54] ENDOSCOPIC PUNCTURE NEEDLE

[75] Inventors: Masatoshi Tonomura, Koganei; Minoru Shinozuka, Hachioji, both of Japan

[73] Assignee: Olympus Optical Co., Ltd., Tokyo, Japan

[21] Appl. No.: 534,298

[22] Filed: Sep. 27, 1995

[30] Foreign Application Priority Data

Sep. 29, 1994 [JP] Japan .................... 6-235588
Aug. 24, 1995 [JP] Japan .................... 7-215716

[51] Int. Cl.$^6$ .................... A61B 17/34
[52] U.S. Cl. .................... 606/185; 606/184; 606/181
[58] Field of Search .................... 606/185, 184, 606/157; 128/753, 754; 604/165, 157, 158, 164, 264

[56] References Cited

U.S. PATENT DOCUMENTS

| | | | |
|---|---|---|---|
| 4,249,541 | 2/1981 | Pratt | 128/753 |
| 4,693,257 | 9/1987 | Markham | 128/752 |
| 4,702,260 | 10/1987 | Wang | 128/753 |
| 4,763,662 | 8/1988 | Yokoi | 128/660 |
| 5,060,658 | 10/1991 | Dejter, Jr. et al. | 128/753 |
| 5,292,310 | 3/1994 | Yoon | 128/753 |
| 5,350,393 | 9/1994 | Yoon | 606/185 |
| 5,360,405 | 11/1994 | Yoon | 606/185 |
| 5,392,790 | 2/1995 | Kanner et al. | 128/753 |

FOREIGN PATENT DOCUMENTS

| | | |
|---|---|---|
| 7838431 | 5/1979 | Germany . |
| 3714064 | 11/1988 | Germany . |
| 4206566A2 | 12/1992 | Germany . |

*Primary Examiner*—Michael Powell Buiz
*Assistant Examiner*—Kevin Truong
*Attorney, Agent, or Firm*—David E. Dougherty

[57] ABSTRACT

An endoscopic puncture needle including a flexible outer sheath, a flexible inner sheath advanceably and retreatably inserted through the outer sheath, and a needle element formed at the distal end of the inner sheath, in which the inner sheath is made of a metallic pipe.

7 Claims, 3 Drawing Sheets

ENDOSCOPIC PUNCTURE NEEDLE

BACKGROUND OF THE INVENTION

1. Field of the Invention

This invention relates to an endoscopic puncture needle to be introduced into a body cavity through a channel of an endoscope for aspiration biopsy, injection or the like.

2. Description of the Related Art

An endoscopic puncture needle of this type is used to make puncture by utilizing a channel of an endoscope, for example, for a biopsy of a tissue in a body cavity. The puncture needle comprises an outer sheath capable of being inserted through the channel of the endoscope, an inner sheath advanceably and retreatably inserted through the outer sheath, and a rigid needle element secured to the distal end of the inner sheath.

When an ultrasonic endoscope is used to stick the needle into a deep-positioned organ, such as the spleen, through a wall of an alimentary canal, such as the stomach and the duodenum, to examine a tissue, the needle element must have a puncture length sufficient to reach the tissue to be examined. Further, since the exit of the channel of the ultrasonic endoscope is positioned at one side of the field of view of the ultrasonic endoscope, the needle element must protrude obliquely toward the organ being observed via an ultrasonic tomography image, so that the protruding amount of the needle element should be large, thus the needle element is required to be as long as possible.

On the other hand, the length of the relatively rigid needle element is limited since the needle element must be advanced and retreated smoothly without being damaged through the relatively small channel of the endoscope when the endoscope is bent.

Under the circumstances, in conventional structures, the needle element tends to have a puncture length insufficient to reach the tissue to be examined. Even if the needle element has a sufficient puncture length, since the needle element connected to the distal end of the inner sheath is long, both of the outer and inner sheaths tend to be incapable of advancing and retreating through the channel when the endoscope is bent and when an treating instrument upheaving member is stood up. Thus, it is possible that a sure puncture operation is not performed.

Further, when an ultrasonic endoscope is used to puncture a deep-positioned organ, such as the spleen, through a wall of an alimentary canal, such as the stomach and the duodenum, to examine a tissue, a force capable of secure puncture of the deep-positioned organ through the alimentary canal must be transmitted to the distal end of the puncture needle. Moreover, the needle element must be advanced and retreated smoothly without being damaged through the channel of the endoscope when the endoscope is bent.

However, in conventional structures, the inner sheath is made of a flexible tube. Therefore, when the inner tube is pushed in to stick the needle element into a deep-positioned tissue, it is possible that the inner sheath made of the flexible tube is flexed within the outer sheath and that the force is not completely transmitted to the distal end of the puncture needle, thus sure puncture may not be accomplished.

SUMMARY OF THE INVENTION

An object of the present invention is to provide an endoscopic puncture needle which has a relatively simple structure and can surely puncture a deep-positioned tissue such as a deep-positioned organ, for example, through an alimentary canal.

An endoscopic puncture needle according to the present invention comprises a flexible outer sheath, a flexible inner sheath advanceably and retreatably inserted through the outer sheath, and a needle element coupled to the distal end of the inner sheath, the inner sheath being made of a metallic pipe member. When the needle element is stuck, the inner sheath is also stuck into a tissue.

Other features and advantages of the present invention will be apparent from the following description.

DETAILED DESCRIPTION OF THE PREFERRED EMBODIMENTS

Referring to FIGS. 1 to 4, a first embodiment of the present invention is described.

Figure 1:
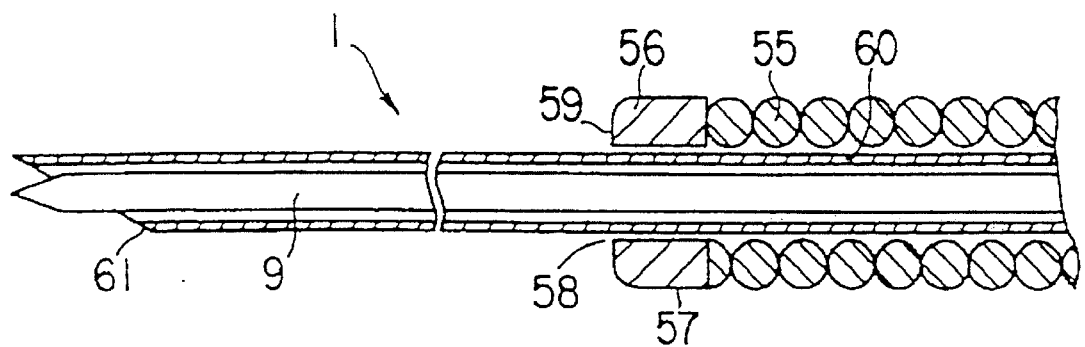
FIG. 1 is a cross-sectional view of the distal end portion of an endoscopic puncture needle according to a first embodiment of the present invention.
Figure 2:
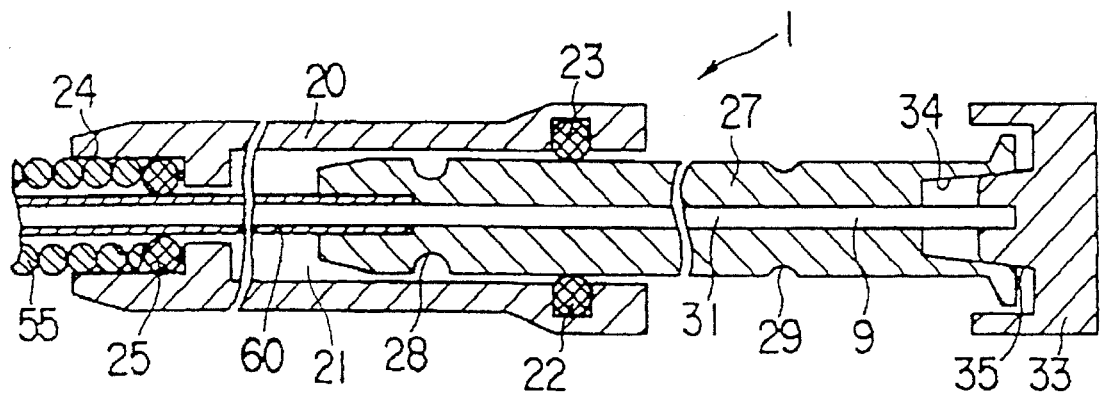
FIG. 2 is a cross-sectional view of the proximal end portion of the endoscopic puncture needle according to the first embodiment.
Figure 3:
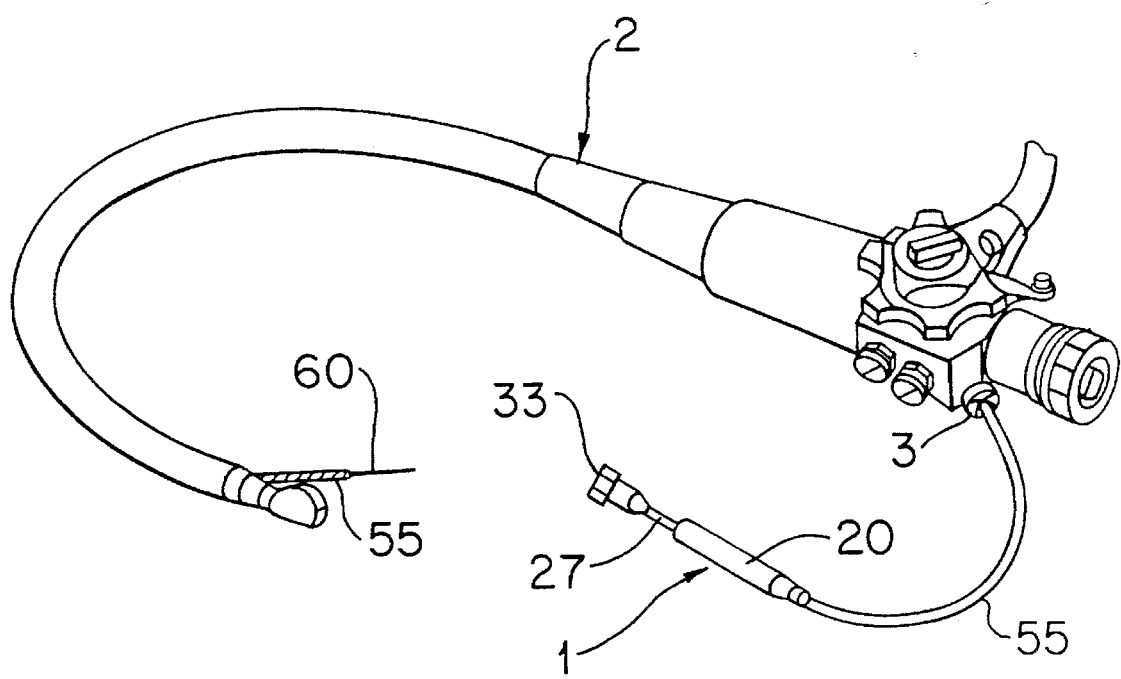
FIG. 3 is a perspective view showing the state in which the endoscopic puncture needle according to the first embodiment is used with an endoscope.
Figure 4:
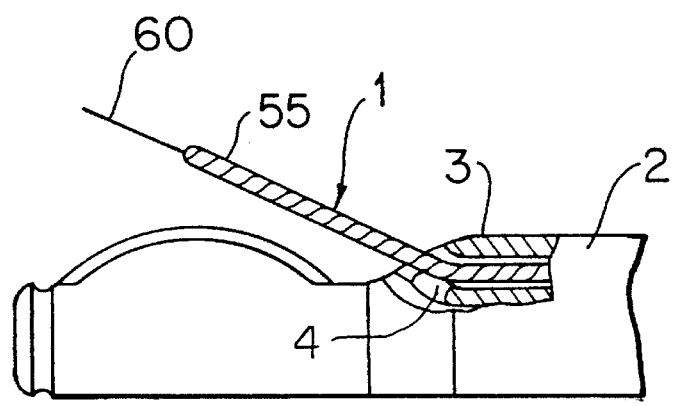
FIG. 4 is an illustration of an upheaving member at an exit of a channel of the endoscope shown in FIG. 3.

FIG. 1 shows the distal end portion of an endoscopic puncture needle 1 and FIG. 2 shows the proximal end portion of the endoscopic puncture needle 1. FIG. 3 illustrates the state in which an inserting body of the endoscopic puncture needle 1 is inserted through an inserting channel 3 of an endoscope 2. FIG. 4 illustrates the state in which the distal end of the endoscopic puncture needle 1 is protruded from an exit of the inserting channel 3 of the endoscope 2 into the field of view of ultrasonic observation via an upheaving member 4.

The endoscopic puncture needle 1 comprises the inserting body having an outer sheath 55 made of a flexible close-wound coil, and an inner sheath 60 advanceably and retreatably inserted through the outer sheath 55. The cross-section of the coil of the outer sheath 55 has a circular shape and the side surfaces of its windings closely abut on each other. A hollow tip member 56 has a flat portion 57 having substantially the same outer shape as the outer sheath 55, and an opening 58 positioned at the distal end of the flat portion 57.

The inner sheath 60 advanceably and retreatably inserted through the outer sheath 55 and the tip portion 56 is made of a metallic pipe member, for example, a flexible pipe made of stainless steel and having an outside diameter of 0.7 mm and a wall thickness of 0.05 mm to 0.15 mm, and is relatively resilient and has a strength sufficient to transmit a pushing force. The inner sheath 60 may be formed out of a superelastic alloy tube which is relatively resilient. The inner tube 60 is provided with a slanting portion 61 by cutting its distal end slantingly. A styler 9 is removably inserted into the inner hollow portion of the inner sheath 60.

As shown in FIG. 2, an operating body 20 made of a relatively thick hollow member is secured to the proximal end of the outer sheath 55. A through bore 21 having an inner cavity is formed inside the operating body 20. A groove-like fixing portion 23 for fixing an elastic O-ring 22 is provided in the inner surface of the proximal end portion of the through bore 21. A stepped bore portion 24 for fitting the proximal end portion of the outer sheath 55 is provided in the distal end portion of the through bore 21. An O-ring 25 is fitted and fixed in the step portion of the bore portion 24.

The inner sheath 60 slides airtightly on the inner surface of the O-ring 25 and moves back and forth in the through bore 21 of the operating body 20. A slider 27 for manual operation is fixed to that portion of the inner sheath 60 which is opposite to a needle portion 61. The slider 27 is manually operated to slide on the inner surface of the O-ring 22 with a friction force produced and move in the axial direction of the operating body 20.

The slider 27 is provided on its periphery with recesses 28 and 29 formed by circumferential grooves and spaced apart from each other in the axial direction. The recess 28 on the distal end side is formed in such a position that when the slider 27 is drawn toward the proximal end, the recess 28 is fittingly engaged with the O-ring 22 and the needle portion 61 is contained in the hollow bore of the outer sheath 55. The rear recess 29 is formed in such a position that when the needle portion 61 is most protruded from the outer sheath 55, the recess 29 is fittingly engaged with the O-ring 22, thus forming a stopper means for controlling the largest protruding amount of the needle portion 61.

A hollow bore 31 communicating with the interior of the inner sheath 60 is formed inside the slider 27. The slider 27 is provided at its proximal end portion with a connecting opening 34, the inner surface of which is tapered. The stylet 9 inserted into the hollow bore 31 is provided at its proximal end with a knob 33, and a tapered fitting portion 35 of the knob 33 is removably fitted into and secured to the connecting opening 34. A syringe or the like (not shown) may be connected to the tapered connecting opening 34. The styler 9 is designed in such a manner that its distal end protrudes a little from the needle portion 61 when it is inserted. In this state, the fitting portion 35 of the knob 33 is fitted into and connected to the connecting opening 34.

The endoscopic puncture needle 1 so constructed is inserted into the channel 3 of the endoscope 2 with the needle portion 61 withdrawn into the interior of the outer sheath 55, and the distal end portion of the endoscopic puncture needle 1 is protruded into the body cavity. When the distal end of the outer sheath 55 is brought near the target position by operating the upheaving member 4 or the like, the slider 27 is pushed in. At that time, the protruding amount of the needle portion 61 is kept constant by the O-ring 22 fitting into the rear recess 29 of the slider 27. When the needle portion 61 protrudes a little from the tip member 56, the upheaving member 4 shown in FIG. 4 is stood up so that the needle portion 61 appears in the ultrasonic image.

In this state, the slider 27 is further pushed in so that the needle portion 61 and the inner sheath 60 are introduced into the tissue. This puncture operation is performed until the needle portion 61 reaches the target position of the deep-positioned tissue. When the needle portion 61 reaches the target position, the stylet 9 is drawn out and a syringe (not shown) is connected to the connecting opening 34 to make aspiration, thereby taking the tissue into the needle portion 61.

According to this first embodiment, the inner sheath 60 is formed by a single thin metallic pipe extending to the proximal end side and the distal end of the inner sheath 60 is the needle portion 61. Therefore, when inner sheath 60 is pushed in for the puncture of a deep-positioned organ, the inner sheath 60 neither buckles in the outer sheath 55 nor bends at the distal end of the outer sheath 55 from which the inner sheath 60 protrudes, so that a puncture force can be transmitted to the distal end for sure puncture. Also, when the forceps upheaving member 4 is stood up, that is, when the outer sheath 55 and the inner sheath 60 bend due to a bending stress applied by the upheaving member 4, the inner sheath 60 is not deformed so that the needle portion 61 can be freely advanced and retreated and the puncture force can be transmitted to the distal end to facilitate the insertion into a tissue of a deep-positioned organ for sure puncture.

Figure 5:
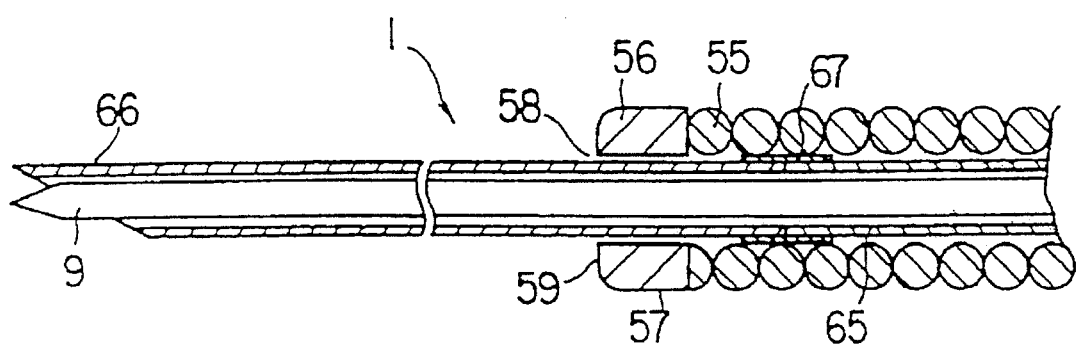
FIG. 5 is a cross-sectional view of the distal end portion of an endoscopic puncture needle according to a second embodiment of the present invention.

Next, referring to FIG. 5, a second embodiment of the present invention is described.

In the second embodiment, a needle element 66 is connected to the distal end of an inner sheath 65, and a coupling tube 67 is fitted on the periphery of the abutting ends of the inner sheath 65 and the needle element 66 to fixed them. The inner sheath 65 is formed by a pipe having a wall thickness of 0.05 mm to 0.15 mm and made of, for example, a stainless steel. The needle element 66 is formed by a pipe having a wall thickness of 0.05 mm to 0.15 mm and the same diameter as the inner sheath 65, and made of, for example, a superelastic alloy. Other features are the same as in the first embodiment and their operations are also the same.

Figure 6:
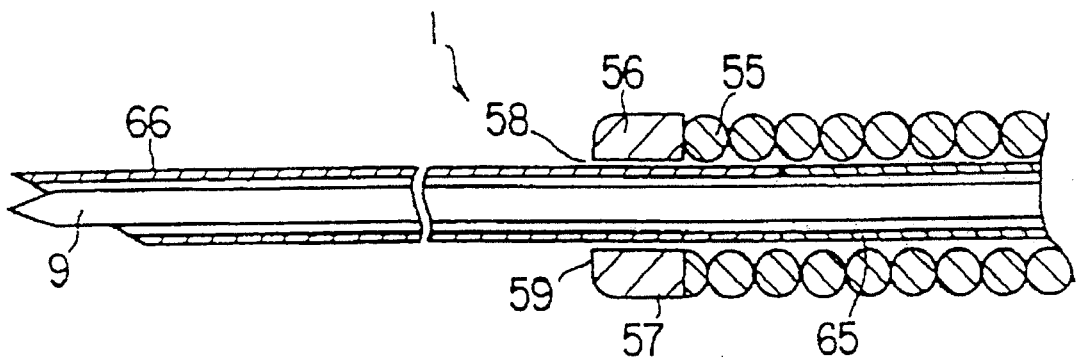
FIG. 6 is a cross-sectional view of the distal end portion of an endoscopic puncture needle according to a third embodiment of the present invention.

According to the second embodiment, in addition to the effects of the first embodiment, since the needle element 66 is made of a superelastic alloy, no permanent deformation of the needle element 66 occurs even if it is repeatedly used or passes through that portion of the outer sheath 55 which is bent by the forceps upheaving member 4o Next, referring to FIG. 6, a third embodiment of the present invention is described. This is a variation of the second embodiment of the present invention.

In the third embodiment, as shown in FIG. 6, a needle element 66 abuts on the distal end of an inner sheath 65 and both members are fixed together by, for example, welding. The inner sheath 65 is formed by a pipe having a wall thickness of 0.05 mm to 0.15 mm and made of, for example, a stainless steel. The needle element 66 has a length of about 5 mm and a wall thickness of 0.2 mm and is made of, for example, a stainless steel. Other features and operations are the same as in the second embodiment.

According to the third embodiment, in addition to the effects of the second embodiment, since the needle element 66 is formed by a stainless steel pipe which is short and has a thick wall, it is not caught on the forceps upheaving member 4 so that smooth and sure puncture can be made. Further, since in coupling the inner sheath 65 and the needle element 66 they are directly fixed together without using a coupling tube, no protruding portion is formed so that also in this aspect it can be smoothly inserted without being caught on the forceps upheaving member 4 and smooth and sure puncture can be made.

It is apparent that widely different embodiments of this invention may be made without departing from the spirit and scope thereof. This invention is not limited by its particular embodiments except that it is defined by the appended claims.

What is claimed is:

1. An endoscopic puncture needle insertable into a channel of an endoscope for aspirating and sampling a tissue in a body cavity, the endoscopic puncture needle insertable into and having a sufficient length to pass through the channel of the endoscope and comprising a flexible outer sheath, a flexible inner sheath advanceably and retreatably inserted through the outer sheath, formed by a metallic pipe and having a distal end, and a needle element formed at the distal end of the inner sheath in which the needle element is separate from the inner sheath and connected to the inner sheath.

2. The endoscopic puncture needle of claim 1, in which the metallic pipe has a wall thickness of 0.05 mm to 0.15 mm.

3. The endoscopic puncture needle of claim 1, in which the needle element is formed by a flexible metallic tube having a wall thickness of 0.05 mm to 0.15 mm.

4. The endoscopic puncture needle of claim 1, in which the metallic tube has a distal end and the needle element is formed by cutting the distal end of the metallic tube slantingly.

5. The endoscopic puncture needle of claim 1, in which the inner sheath is formed such that a stylet can be removably inserted into the inner sheath.

6. The endoscopic puncture needle of claim 1, for use with an ultrasonic endoscope which forms an ultrasonic tomographic image of the field of view of ultrasonic observation, in which the puncture needle includes means for biasing said needle element toward the field of view of ultrasonic observation.

7. An endoscopic puncture needle comprising a flexible outer sheath, a flexible inner sheath advanceably and retreatably inserted through the outer sheath, formed by a metallic pipe and having a distal end, and a needle element formed at the distal end of the inner sheath in which said needle element is separate from the inner sheath and connected to said inner sheath, and wherein said needle element is made of a superelastic alloy.

* * * * *